United States Patent
Cross et al.

(10) Patent No.: US 7,615,050 B2
(45) Date of Patent: Nov. 10, 2009

(54) SYSTEMS AND METHODS FOR CREATING A LESION USING TRANSJUGULAR APPROACH

(75) Inventors: Jeffrey M. Cross, Charlestown, MA (US); Paul DiCarlo, Middleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 615 days.

(21) Appl. No.: 11/168,234

(22) Filed: Jun. 27, 2005

(65) Prior Publication Data

US 2006/0293738 A1 Dec. 28, 2006

(51) Int. Cl.
*A61B 18/14* (2006.01)

(52) U.S. Cl. .................................. 606/41; 606/167

(58) Field of Classification Search .............. 606/37, 606/41, 167, 48–50; 604/22; 607/122; 514/44
See application file for complete search history.

(56) References Cited

U.S. PATENT DOCUMENTS

| | | | |
|---|---|---|---|
| 5,254,088 A | 10/1993 | Lundquist et al. | |
| 5,273,535 A | 12/1993 | Edwards et al. | |
| 5,336,182 A | 8/1994 | Lundquist et al. | |
| 5,358,478 A | 10/1994 | Thompson et al. | |
| 5,364,351 A | 11/1994 | Heinzelman et al. | |
| 5,395,327 A | 3/1995 | Lundquist et al. | |
| 5,456,664 A | 10/1995 | Heinzelman et al. | |
| 5,531,686 A | 7/1996 | Lundquist et al. | |
| 5,536,240 A * | 7/1996 | Edwards et al. | 604/22 |
| 5,707,350 A * | 1/1998 | Krause et al. | 604/22 |
| 5,855,576 A | 1/1999 | LeVeen et al. | |
| 5,906,606 A * | 5/1999 | Chee et al. | 604/527 |
| 6,033,378 A | 3/2000 | Lundquist et al. | |
| 6,080,149 A | 6/2000 | Huang et al. | |
| 6,283,951 B1 * | 9/2001 | Flaherty et al. | 604/529 |
| 6,287,304 B1 * | 9/2001 | Eggers et al. | 606/37 |
| 6,485,455 B1 | 11/2002 | Thompson et al. | |
| 6,500,175 B1 * | 12/2002 | Gough et al. | 606/42 |

(Continued)

FOREIGN PATENT DOCUMENTS

EP 0628288 A2 5/1994

(Continued)

OTHER PUBLICATIONS

PCT International Preliminary Report on Patentability for PCT/US2006/021715, Applicant: Boston Scientific Scimed, Inc., Form PCT/IB/326, dated Jan. 17, 2008 (6 pages).

(Continued)

*Primary Examiner*—Michael Peffley
*Assistant Examiner*—Samantha Muro
(74) *Attorney, Agent, or Firm*—Vista IP Law Group LLP

(57) ABSTRACT

A method of treating a tissue region includes inserting a flexible sheath within a vessel, the vessel leading to a tissue region, placing a distal end of the sheath through a wall of the vessel to thereby position the distal end is at or adjacent the tissue region, deploying a plurality of electrodes from the distal end of the sheath such that tips of the deployed electrodes approximately face towards a proximal end, and delivering energy to the tissue region using the deployed electrodes.

19 Claims, 4 Drawing Sheets

U.S. PATENT DOCUMENTS

| | | | |
|---|---|---|---|
| 7,317,950 B2 * | 1/2008 | Lee | 607/122 |
| 2003/0060817 A1 * | 3/2003 | Sauvageau et al. | 606/32 |
| 2003/0212394 A1 * | 11/2003 | Pearson et al. | 606/41 |
| 2004/0098075 A1 * | 5/2004 | Lee | 607/122 |
| 2004/0236360 A1 * | 11/2004 | Cohn et al. | 606/167 |
| 2005/0020965 A1 * | 1/2005 | Rioux et al. | 604/21 |
| 2005/0234399 A1 * | 10/2005 | Wood, Jr. | 604/65 |
| 2006/0089635 A1 * | 4/2006 | Young et al. | 606/41 |
| 2006/0154884 A1 * | 7/2006 | Buchwald | 514/44 |
| 2006/0217704 A1 * | 9/2006 | Cockburn et al. | 606/41 |
| 2006/0224154 A1 * | 10/2006 | Shadduck et al. | 606/41 |

FOREIGN PATENT DOCUMENTS

| | | |
|---|---|---|
| GB | 2313062 A | 11/1997 |

OTHER PUBLICATIONS

PCT International Search Report for PCT/US2006/021715, Applicant: Boston Scientific Scimed, Inc., Form PCT/ISA/210 and 220, dated Nov. 21, 2006(5 pages).

PCT Written Opinion of the International Search Authority for PCT/US2006/021715, Applicant: Boston Scientific Scimed, Inc., Form PCT/ISA/237, dated Nov. 21, 2006 (4 pages).

* cited by examiner

SYSTEMS AND METHODS FOR CREATING A LESION USING TRANSJUGULAR APPROACH

BACKGROUND

1. Field

The field of the invention relates to medical devices, and more particularly, to medical devices and methods of their use for treating tumors or other targeted bodily tissue using electrical energy.

2. Background

Tissue may be destroyed, ablated, or otherwise treated using thermal energy during various therapeutic procedures. Many forms of thermal energy may be imparted to tissue, such as radio frequency electrical energy, microwave electromagnetic energy, laser energy, acoustic energy, or thermal conduction.

In particular, radio frequency ablation (RFA) may be used to treat patients with tissue anomalies, such as liver anomalies and many primary cancers, such as cancers of the stomach, bowel, pancreas, kidney and lung. RFA treatment involves the destroying undesirable cells by generating heat through agitation caused by the application of alternating electrical current (radio frequency energy) through the tissue.

Various RF ablation devices have been suggested for this purpose. For example, U.S. Pat. No. 5,855,576 describes an ablation apparatus that includes a plurality of wire electrodes. Each of the wires includes a proximal end that is coupled to a generator; and a distal end that may project from a distal end of a cannula. The wires are arranged in an array with the distal ends located generally radially and uniformly spaced apart from the catheter distal end. The wires may be energized in a monopolar or bipolar configuration to heat and necrose tissue within a precisely defined volumetric region of target tissue. The current may flow between closely spaced wire electrodes (bipolar mode) or between one or more wire electrodes and a larger, common electrode (monopolar mode) located remotely from the tissue to be heated. To assure that the target tissue is adequately treated and/or to limit damaging adjacent healthy tissues, the array of wires may be arranged uniformly, e.g., substantially evenly and symmetrically spaced-apart so that heat is generated uniformly within the desired target tissue volume. Such devices may be used either in open surgical settings, in laparoscopic procedures, and/or in percutaneous interventions.

Currently, tumor near a vessel may be difficult to ablate. This is because the vessel continuously provide blood to the tumor during an ablation procedure, thereby carrying heat away from a targeted region. As a result, it may be difficult to achieve a complete burn for the tumor near the vessel.

SUMMARY

In accordance with some embodiments, a method of treating a tissue region includes inserting a flexible sheath within a vessel, the vessel leading to a tissue region, placing a distal end of the sheath through a wall of the vessel to thereby position the distal end at or adjacent the tissue region, deploying a plurality of electrodes from the distal end of the sheath such that tips of the deployed electrodes approximately face towards a proximal end, and delivering energy to at least a portion of the tissue region using the deployed electrodes.

In accordance with other embodiments, a system for treating tissue within a tissue region using electrical energy includes a flexible sheath having a proximal end, a distal end, and a body extending between the proximal and the distal ends, wherein the body is sized such that it can be placed within a blood vessel, and has a length such that when placed within the blood vessel, the proximal end is outside a patient's body and the distal end is adjacent the tissue region, and an array of electrodes slidably disposed within a lumen of the sheath, wherein the sheath further has a sharp distal tip for puncturing a vessel.

In other embodiments, a system for treating tissue within a tissue region using electrical energy includes a flexible sheath having a proximal end, a distal end, and a body extending between the proximal and the distal ends, wherein the body is sized such that it can be placed within a blood vessel, and has a length such that when placed within the blood vessel, the proximal end is outside a patient's body and the distal end is adjacent the tissue region, a shaft having a body, the body having a wall and a plurality of openings through the wall, and an array of electrodes coupled to the shaft, and slidably disposed within a lumen of the sheath.

Other aspects and features will be evident from reading the following detailed description of the embodiments.

BRIEF DESCRIPTION OF THE DRAWINGS

The drawings illustrate the design and utility of the illustrated embodiments, in which similar elements are referred to by common reference numerals. In order to better appreciate how advantages and objects of the embodiments are obtained, a more particular description of the embodiments is illustrated in the accompanying drawings.

DETAILED DESCRIPTION OF THE EMBODIMENTS

Figure 1:
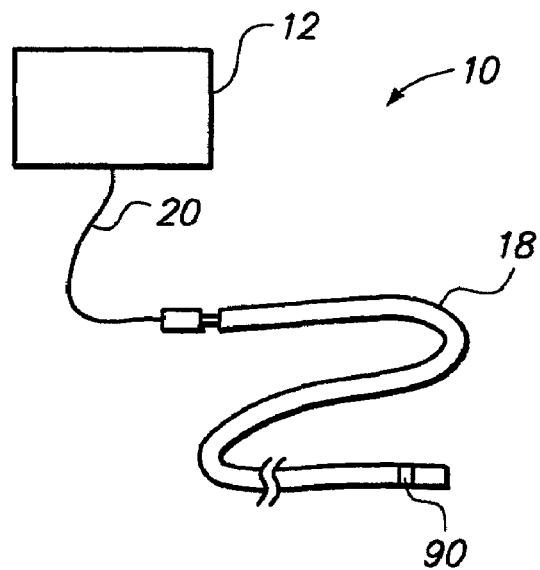
FIG. 1 illustrates a system for delivering electrical energy to tissue in accordance with some embodiments.

FIG. 1 shows an ablation system 10, in accordance with some embodiments. The ablation system 10 includes a source of energy 12, e.g., a radio frequency (RF) generator, and an ablation device 18 configured to be coupled to the generator 12 via a cable 20 during use.

The generator 12 is preferably capable of operating with a fixed or controlled voltage or current so that power and current diminish as impedance of the tissue being ablated increases. Exemplary generators are described in U.S. Pat. No. 6,080,149, the disclosure of which is expressly incorporated by reference herein. The preferred generator 12 may operate at relatively low fixed voltages, typically below one hundred fifty volts (150 V) peak-to-peak, and preferably between about fifty and one hundred volts (50-100 V). Such radio frequency generators are available from Boston Scientific Corporation, assignee of the present application, as well as from other commercial suppliers. It should be noted that the generator 12 is not limited to those that operate at the range of voltages discussed previously, and that generators capable of operating at other ranges of voltages may also be used.

Figure 2:
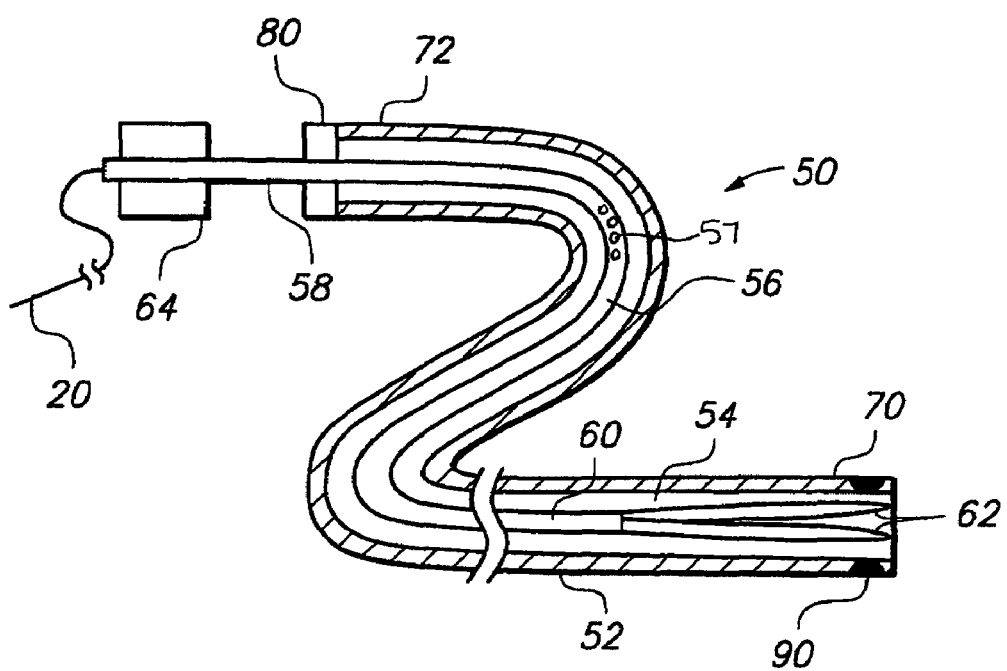
FIG. 2 is a cross-sectional side view of an embodiment of an ablation device, showing electrode tines constrained within a sheath.
Figure 3:
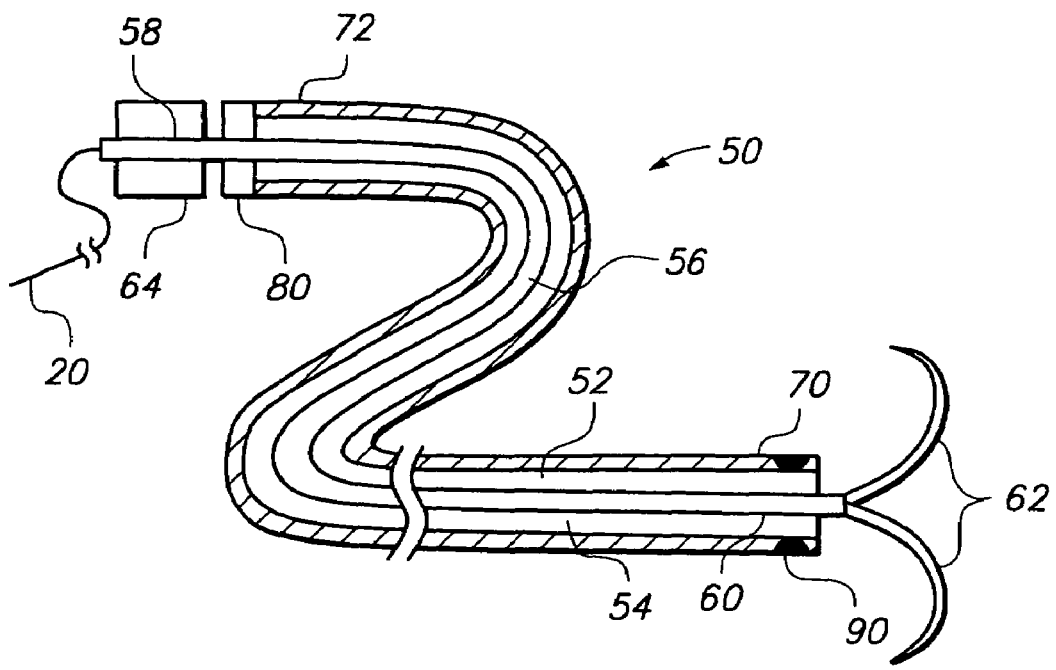
FIG. 3 is a cross-sectional side view of the ablation device of FIG. 2, showing the electrode tines deployed from the sheath.

Turning to FIGS. 2 and 3, in the illustrated embodiments, the ablation device 18 of FIG. 1 is a ablation assembly 50 that includes a sheath 52 having a lumen 54, a shaft 56 having a proximal end 58 and a distal end 60, and a plurality of electrode tines (or wires) 62 secured to the distal end 60 of the shaft 56. The proximal end 58 of the shaft 56 may include a connector (not shown) for coupling to the generator 12. Alternatively, the ablation assembly 50 may itself include a cable (not shown) on the proximal end 58 of the shaft 56, and a connector may be provided on the proximal end of the cable (not shown).

In the illustrated embodiments, the sheath 52 has a length between about forty and one hundred and thirty centimeters (40-130 cm), and more preferably, between sixty and eighty (60-80 cm). Also, the sheath 52 has an outer diameter or cross sectional dimension between about one and five millimeters (1-5 mm), and more preferably, between two and four millimeters (2-4 mm). In one implementation, the sheath 52 is configured (e.g., sized and shaped) such that it can be inserted within a vessel (e.g., a jugular vein), and that a body of the cannula 52 can extend between a proximal end 72 located outside a patient's body and a distal end 70 located at or adjacent a target region, e.g., a liver, when the sheath 52 is inserted into a jugular vein. In other embodiments, the sheath 52 may also have other lengths and outer cross sectional dimensions, depending upon the application. The sheath 52 may be formed from a polymer, and the like, as long as it is sufficiently flexible for allowing the sheath 52 to be steered through a vessel. The sheath 52 may be electrically active or inactive, depending upon the manner in which electrical energy is to be applied.

The sheath 52 coaxially surrounds the shaft 56 such that the shaft 56 may be advanced axially from or retracted axially into the lumen 54 of the sheath 52. The shaft 56 can be made from any of a variety of elastic materials, such as a polymer, or a metal, as long as it is sufficiently elastic to be steered through a vessel. For example, the shaft 56 can be a Nitinol tube having a plurality of openings 57 for providing a desired flexibility for the tube, which is available at Boston Scientific Corporation, the Precision Vascular Division. In other cases, instead of being a tube, the shaft 56 can have a solid cross-section. Optionally, a handle 64 may be provided on the proximal end 58 of the shaft 56 to facilitate manipulating the shaft 56. The electrode tines 62 are compressed into a low profile when disposed within the lumen 54 of the sheath 52, as shown in FIG. 2. As shown in FIG. 3, the proximal end 58 of the shaft 56 or the handle 64 (if one is provided) can be advanced to deploy the wires 62 from the lumen 54 of the sheath 52. When the electrode tines 62 are unconfined outside the lumen 54 of the sheath 52, they assume a relaxed expanded configuration. FIG. 3 shows an exemplary two-wire array including electrode tines 62 biased towards a generally "U" shape and substantially uniformly separated from one another about a longitudinal axis of the shaft 56. Alternatively, each electrode tine 62 may have other shapes, such as a "J" shape, a flare shape, a bent shape, a parabolic shape, and/or the array may have one electrode tine 62 or more than two electrode tines 62. The array may also have non-uniform spacing to produce an asymmetrical lesion. In some embodiments, the electrode tines 62 are formed from spring wire, superelastic material, or other material, such as Nitinol, that may retain a shape memory. During use of the ablation assembly 50, the electrode tines 62 are deployed into a target tissue region to deliver energy to the tissue to create a lesion. Ablation devices having a spreading array of electrode tines have been described in U.S. Pat. No. 5,855,576, the disclosure of which is expressly incorporated by reference herein.

Optionally, a marker (not shown) may be placed on the handle 64 and/or on the proximal end 58 of the shaft 56 for indicating a rotational orientation of the shaft 56 during use. In other embodiments, the ablation assembly 50 may also carry one or more radio-opaque markers (not shown) to assist positioning the ablation assembly 50 during a procedure, as is known in the art. For example, in some embodiments, the ablation assembly 50 may further include a radio opaque marker located at a distal end 70 of the sheath 52 or the shaft 56. Alternatively or additionally, one or more of the electrode tines 62 may each carry a radio opaque element (e.g., a marker). Optionally, the ablation assembly 50 may also include a sensor, e.g., a temperature sensor and/or an impedance sensor (not shown), carried by the distal end of the shaft 56 and/or one or more of the electrode tines 62. In such cases, the energy source 12 may be configured to control an amount of energy delivered to the electrode tines 62 based at least in part on a signal provided by the sensor.

In the illustrated embodiments, the ablation assembly 50 further include a steering mechanism 80 secured to the proximal end 72 of the sheath 52 for steering a distal end 70 of the sheath 52. The steering mechanism 80 includes a rotatable cam and one or more steering wires (not shown) connected between the cam and the distal end 70 of the sheath 52. During use, the cam can be rotated to apply tension to a steering wire, thereby causing the distal end 70 of the sheath 52 to bend. Further details regarding the steering mechanism 80 are described in U.S. Pat. No. 5,273,535, the entire disclosure of which is herein incorporated by reference. Steering devices that can be used with the ablation assembly 50 have also been described in U.S. Pat. Nos. 5,254,088, 5,336,182, 5,358,478, 5,364,351, 5,395,327, 5,456,664, 5,531,686, 6,033,378, and 6,485,455, the entire disclosures of which are expressly incorporated by reference herein.

In other embodiments, the ablation assembly 50 does not include the steering mechanism 80. In such cases, a separate introducer sheath or introducer catheter may be used to gain access through a vessel. The introducer sheath may have a pre-bent distal end for assisting steering through a vessel. Alternatively, the introducer sheath may be steered using a guidewire in a conventional manner, or may include a steering mechanism, such as the steering mechanism 80 discussed previously, for steering its distal end. In some embodiments, the introducer sheath/catheter can have a sharp distal tip for piercing tissue.

In other embodiments, the ablation assembly 50 can include a guidewire (not shown) to assist placement of the distal end 70 of the sheath 52 in a conventional manner. The guidewire may be located within the lumen 54 of the sheath 52, or alternatively, located within another lumen (not shown) in the sheath 52 that is parallel to the lumen 54.

It should be noted that the ablation device 18 is not necessarily limited to the ablation assembly 50 shown in FIGS. 2 and 3, and that the ablation device 18 may be selected from a variety of devices that are capable of delivering ablation or therapeutic energy. For example, medical devices may also be used that are configured for delivering ultrasound energy, microwave energy, and/or other forms of energy for the purpose of ablation, which are well known in the art.

Figure 4:
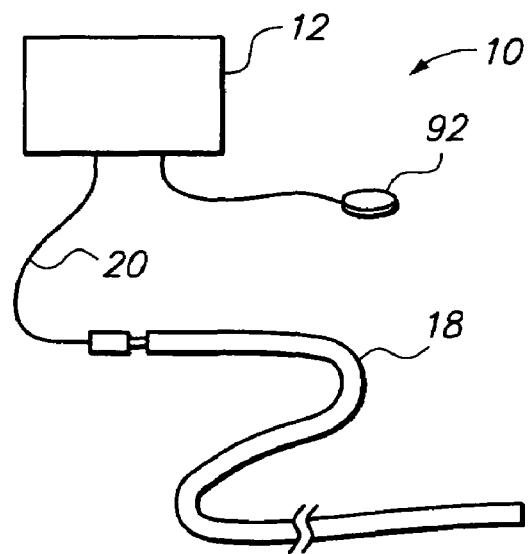
FIG. 4 illustrates a system for delivering electrical energy to tissue in accordance with other embodiments.

In the illustrated embodiments, the ablation assembly 50 also includes an electrode 90 secured to the sheath 52. A wire (not shown) may be disposed within the wall of the sheath 52 to electrically couple the electrode 90 to the generator 12 during use. The electrode 90 and the array of electrodes 62 are connected to opposite terminals of the generator 12 for delivering energy to target tissue in a bipolar mode. In other embodiments, the ablation assembly 50 does not include the electrode 90 (FIG. 4). In such cases, the system 10 further includes an electrode pad 92 electrically coupled to the generator 12. The electrode pad 92 functions as a return electrode, and operates in conjunction with the ablation assembly 50 to deliver energy to target tissue in a monopolar mode.

Figure 5A:
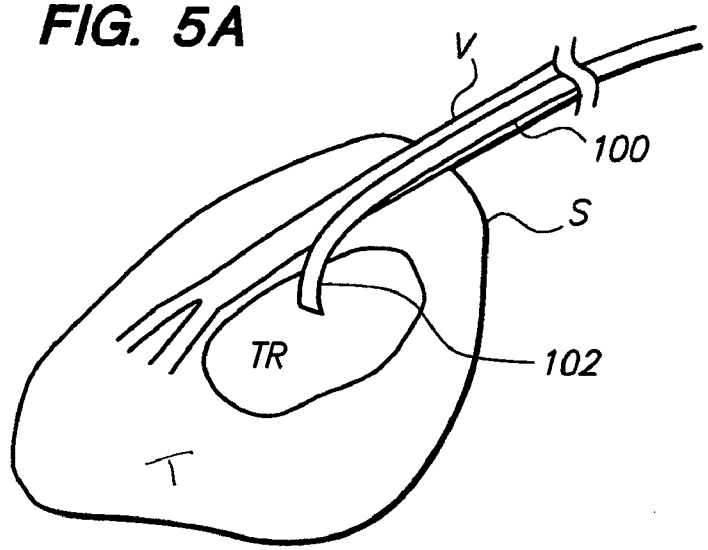
FIGS. 5A-5D are cross-sectional views, showing a method for treating tissue, in accordance with some embodiments.
Figure 5B:
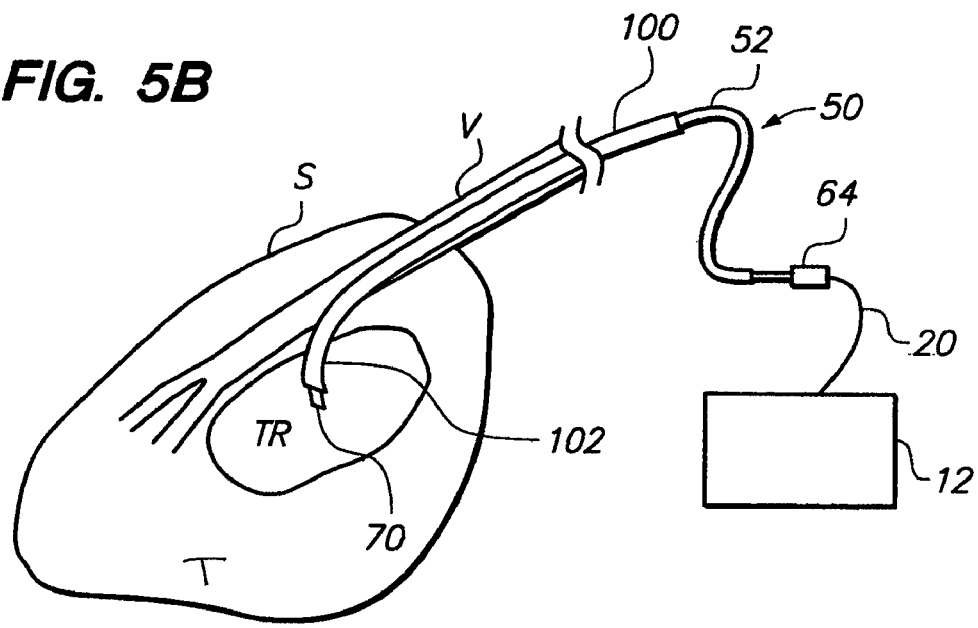

Referring now to FIGS. 5A-5D, the ablation system 10 may be used to treat at least a portion, e.g., a target tissue TS, within a treatment region TR within tissue T located beneath skin or an organ surface S of a patient. First, if an introducer sheath/catheter 100 is provided, the introducer sheath 100 can be inserted through a patient's skin and into a vessel V. The introducer sheath 100 is then steered through the vessel V in a conventional manner (e.g., using a guidewire or a steering mechanism) until its distal end 102 is at or adjacent to the treatment region TR. As shown in FIG. 5A, the sharp distal tip of the introducer sheath 100 can then be used to puncture the vessel V to gain access to the treatment region TR. Next, the ablation assembly 50 is inserted into the introducer sheath 100, and is advanced until the distal end 70 of the sheath 52 of the ablation assembly 50 reaches the treatment region TR (FIG. 5B).

In other embodiments, instead of using an introducer sheath/catheter 100, if the ablation assembly 50 includes the steering mechanism 80, the ablation assembly 50 can be inserted through a patient's skin and into the vessel V, and be steered to a desired location at or adjacent to the target region TR. In one implementation, a transjugular approach may be used, in which the distal end 70 is inserted through a jugular vein in the patient's neck. After the distal end 70 of the sheath 52 has been inserted through the patient's skin, the distal end 70 is then steered to the tissue T, such as a liver tissue, through the vessel V. The sheath 52 may be steered by using the guidewire in a conventional manner, or by applying tension to steering wire(s) (if the steering mechanism 80 is provided). If the sheath 52 has a sharp distal tip, it can be used to puncture the vessel V to allow the distal end 70 of the sheath 52 to gain access to the target region TR. In other embodiments, a separate puncturing device, such as a wire or a needle, can be inserted through the sheath 52 to puncture the vessel V.

Figure 5C:
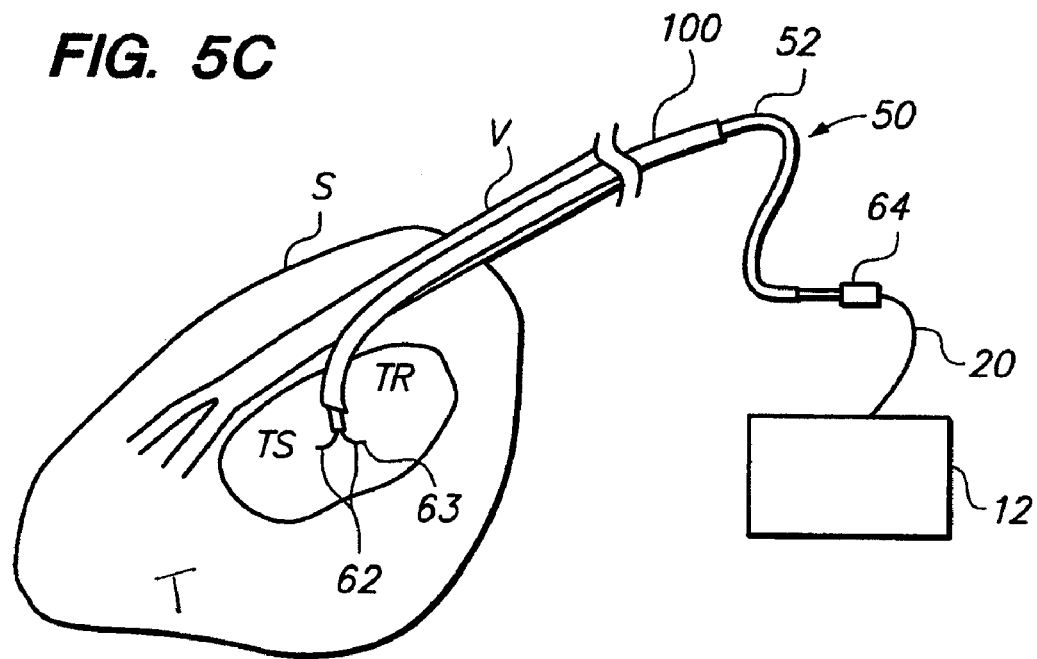
Figure 5D:
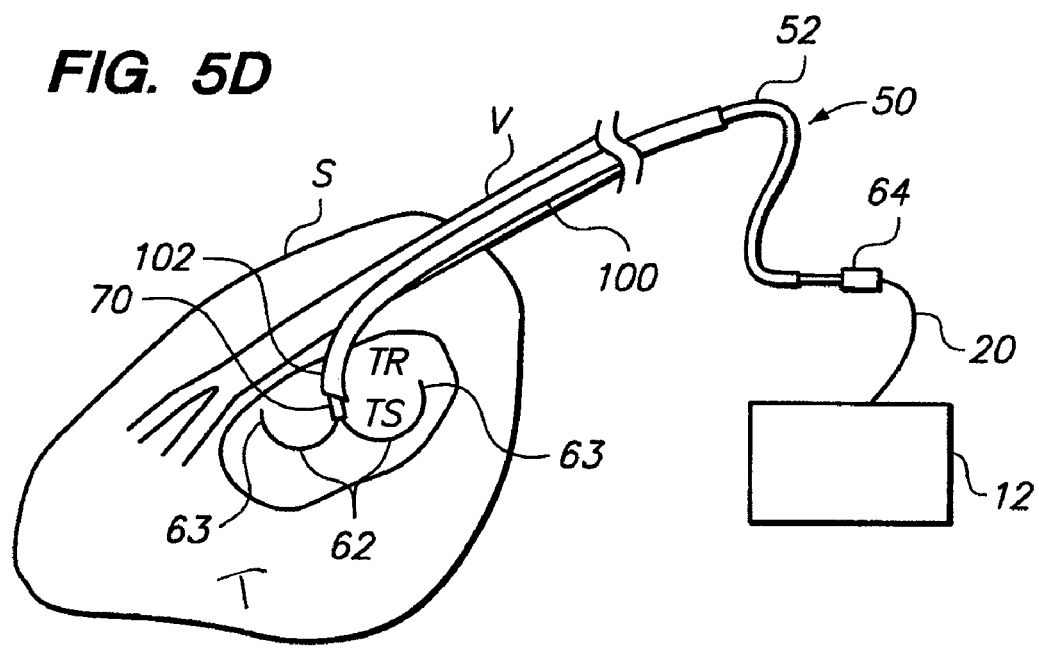

Turning to FIG. 5C, after the sheath 52 is properly placed, the shaft 56 of the ablation assembly 50 is then advanced distally, thereby deploying the array of electrode tines 62 from the distal end 70 of the sheath 52 into the target tissue TS at the target region TR. As illustrated, delivering the electrode tines 62 via the vessel V that leads to the target region TR is advantageous in that, if any bleeding occurs at the target region TR, it will do so back into the vessel V. In the illustrated embodiments, the electrode tines 62 are deployed such the electrode tines 62 are located in close proximity (e.g., within 0.1 millimeter (mm) to 10 mm) to the vessel V. In such arrangement, the distal ends of the electrode tines 62 are positioned among or around sub-branches (not shown) of the vessel V, thereby allowing ablation energy to be effectively delivered to the target tissue TS while minimizing, or at least reducing, the effect of the heat sink due to blood delivered to or from the target region TR. As shown in the figure, the distal ends 63 of the deployed electrode tines 62 are distal to the distal end of the vessel V. Alternatively, the distal ends 63 of the deployed electrode tines 62 may be proximal to the distal end of the vessel V such that the deployed electrode tines 62 at least partially circumscribe a portion of the vessel V. Preferably, the electrode tines 62 are biased to curve radially outwardly as they are deployed from the sheath 52. The shaft 56 of the ablation device 18 may be advanced sufficiently such that the electrode tines 62 fully deploy to circumscribe substantially tissue within the target tissue TS of treatment region TR, as shown in FIG. 5D. Alternatively, the electrode tines 62 may be only partially deployed or deployed incrementally in stages during a procedure.

Next, energy, preferably RF electrical energy, may be delivered from the generator 12 to the wires 62 of the ablation device 18, thereby substantially creating a lesion at the target tissue TS of the treatment region TR. If the system of FIG. 1 is used, the electrode 90 and the electrodes 62 will operate to deliver ablation energy in a bipolar mode. In such cases, ablation energy will flow between the electrode 90 and the array of electrodes 62. Alternatively, if the system of FIG. 4 is used, the electrode pad 92 may be coupled to the opposite terminal (not shown) of the generator 12, and is placed on the patient's skin in a conventional manner. In such cases, ablation energy will flow between the electrode pad 92 and the electrodes 62, thereby delivering ablation energy in a monopolar manner. As shown in the figure, the deployed electrodes 62 have distal ends 63 that point at least partially towards a proximal end (e.g., a component of the vector representing the direction in which the distal ends 63 point is towards a proximal end—e.g., towards the vessel V). Such configuration allows the ablation energy to be effectively delivered to the target tissue TS while minimizing, or at least reducing, the heat sink effect resulted from blood flowing to or from the vessel V.

When a desired lesion at the target tissue TS of the treatment region TR has been created, the electrode tines 62 of the ablation device 18 may be retracted into the lumen 54 of the sheath 52, and the ablation device 18 may be removed from the treatment region TR. In some cases, the entire treatment region TR may be ablated in a single pass. In other cases, if it is desired to perform further ablation to increase the lesion size or to create lesions at different site(s), e.g., at other target tissue TS, within the treatment region TR or elsewhere, the electrode tines 62 of the ablation device 18 may be introduced and deployed at different target site(s), and the same steps discussed previously may be repeated.

Although particular embodiments have been shown and described, it will be understood that it is not intended to limit the present inventions to the preferred embodiments, and it will be obvious to those skilled in the art that various changes and modifications may be made without departing from the spirit and scope of the present inventions. For example, the electrode tines 62 may be a single electrode made from a plurality of conductive components, or a plurality of electrodes. As such, the term, "a plurality of electrodes" should not be limited to more than one electrode, and may include a single electrode having a plurality of conductive components/parts. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A method of treating a tissue region, comprising:
   inserting a flexible sheath within a blood vessel, the blood vessel leading to a tissue region;
   placing a distal end of the sheath through a wall of the blood vessel to thereby position the distal end at or adjacent the tissue region;
   deploying a plurality of electrodes from the distal end of the sheath such that tips of the deployed electrodes approximately face towards a proximal end and such that the electrodes are located 0.1-10 mm away from the wall of the blood vessel; and
   delivering energy to at least a portion of the tissue region using the deployed electrodes.

2. The method of claim 1, wherein the tissue region comprises at least a portion of a liver.

3. The method of claim 1, wherein the blood vessel comprises a jugular vein.

4. The method of claim 1, wherein the placing comprises using a guidewire.

5. The method of claim 1, wherein the placing comprises using the sheath to puncture the blood vessel.

6. The method of claim 1, wherein the placing comprises using an introducer sheath to puncture the blood vessel, and inserting the flexible sheath into the introducer sheath.

7. The method of claim 1, wherein the delivered energy comprises radiofrequency energy.

8. The method of claim 1, wherein the energy is delivered until a lesion is formed at a portion of the tissue region.

9. The method of claim 1, wherein the plurality of electrodes comprises a plurality of electrode tines.

10. The method of claim 1, wherein the plurality of electrodes each has a curvilinear shape.

11. The method of claim 1, further comprising retaining a proximal end of the sheath outside of a patient's body.

12. The method of claim 1, wherein the deploying the plurality of electrodes comprises distally advancing a shaft relative to the sheath, wherein the shaft is disposed within a lumen of the sheath and the plurality of electrodes are attached to a distal end of the shaft.

13. The method of claim 1, further comprising retracting the plurality of electrodes into the sheath and removing the sheath from the tissue region.

14. The method of claim 13, wherein the retracting comprises proximally retracting a shaft relative to the sheath, wherein the shaft is disposed within a lumen of the sheath and the plurality of electrodes are attached to a distal end of the shaft.

15. The method of claim 1, further comprising steering the flexible sheath within the blood vessel using a steering mechanism coupled to a proximal end of the flexible sheath.

16. The method of claim 1, wherein the delivering energy comprises delivering energy in a bipolar mode between the plurality of deployed electrodes and an electrode attached to the distal end of the sheath.

17. The method of claim 1, wherein the delivering energy comprises delivering energy in a monopolar mode between the plurality of deployed electrodes and an electrode pad placed on a patient's skin.

18. The method of claim 1, wherein the placing comprises inserting a puncturing device through the flexible sheath and puncturing the wall of the blood vessel using the puncturing device.

19. The method of claim 1, wherein the deploying comprises partially circumscribing a portion of the blood vessel.

* * * * *

UNITED STATES PATENT AND TRADEMARK OFFICE
CERTIFICATE OF CORRECTION

PATENT NO. : 7,615,050 B2 Page 1 of 1
APPLICATION NO. : 11/168234
DATED : November 10, 2009
INVENTOR(S) : Cross et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1116 days.

Signed and Sealed this

Nineteenth Day of October, 2010

David J. Kappos
*Director of the United States Patent and Trademark Office*